// United States Patent //

(12) United States Patent
Nakamura

(10) Patent No.: US 10,228,530 B2
(45) Date of Patent: Mar. 12, 2019

(54) STAND APPARATUS FOR SURGICAL MICROSCOPE

(71) Applicant: MITAKA KOHKI CO., LTD., Tokyo (JP)

(72) Inventor: Katsuyuki Nakamura, Tokyo (JP)

(73) Assignee: MITAKA KOHKI CO., LTD., Tokyo (JP)

( * ) Notice: Subject to any disclaimer, the term of this patent is extended or adjusted under 35 U.S.C. 154(b) by 0 days.

(21) Appl. No.: 15/717,007

(22) Filed: Sep. 27, 2017

(65) Prior Publication Data

US 2018/0095234 A1   Apr. 5, 2018

(30) Foreign Application Priority Data

Sep. 30, 2016   (JP) .................................. 2016-192813
Dec. 6, 2016    (JP) .................................. 2016-236371

(51) Int. Cl.
*G02B 7/00*     (2006.01)
*G02B 21/00*    (2006.01)
*A61B 90/25*    (2016.01)

(52) U.S. Cl.
CPC ............. *G02B 7/001* (2013.01); *A61B 90/25* (2016.02); *G02B 21/0012* (2013.01)

(58) Field of Classification Search
CPC .... G02B 7/001; G02B 21/0012; A61B 90/25; B25J 19/002
USPC .......................... 248/280.11, 282.1, 292.11; 414/744.3–744.5; 74/490.01–490.05
See application file for complete search history.

(56) References Cited

U.S. PATENT DOCUMENTS

| | | | | |
|---|---|---|---|---|
| 3,396,931 A | * | 8/1968 | Eckstein | F16B 7/00 248/280.11 |
| 3,721,416 A | * | 3/1973 | Goudreau | B66C 23/005 248/325 |
| 4,140,226 A | * | 2/1979 | Richter | B25J 9/046 414/729 |
| 4,339,100 A | * | 7/1982 | Heller | F16M 11/08 248/123.2 |
| 5,173,802 A | * | 12/1992 | Heller | F16M 11/08 359/384 |
| 5,536,135 A | * | 7/1996 | Robertson | B65G 47/912 414/728 |
| 5,713,545 A | * | 2/1998 | Nakamura | F16M 11/126 248/123.2 |
| 6,045,104 A | * | 4/2000 | Nakamura | F16M 11/10 248/123.11 |
| 6,702,805 B1 | * | 3/2004 | Stuart | B25J 9/1065 600/102 |

(Continued)

FOREIGN PATENT DOCUMENTS

JP    4628060    11/2010

*Primary Examiner* — Muhammad Ijaz
(74) *Attorney, Agent, or Firm* — Greenblum & Bernstein, P.L.C.

(57) ABSTRACT

A stand apparatus for a surgical microscope includes a stand body and a parallel linkage. The parallel linkage is rotatably attached to the stand body by attaching a lower-end joint thereof instead of a vertical intermediate part thereof to the stand body. When the parallel linkage is tilted frontward, no part of the parallel linkage protrudes rearward. Weight balance of the frontward tilted parallel linkage is maintained by, instead of a counterweight, a compression spring arranged along a rear sub-arm.

3 Claims, 4 Drawing Sheets

(56) References Cited

U.S. PATENT DOCUMENTS

| | | | | |
|---|---|---|---|---|
| 6,748,819 B2* | 6/2004 | Maeguchi | ............... | B25J 9/1065 414/735 |
| 8,910,913 B2* | 12/2014 | Hirose | ................ | A61B 1/00149 248/123.11 |
| 9,375,837 B2* | 6/2016 | Nakamura | ............... | B25J 9/1065 |
| 2003/0066373 A1* | 4/2003 | Maeguchi | ............... | B25J 9/1065 74/490.01 |
| 2003/0151805 A1* | 8/2003 | Schmidt | ................. | A61B 90/25 359/384 |
| 2006/0196299 A1* | 9/2006 | Taboada | ................. | B25J 9/1065 74/490.01 |
| 2009/0020666 A1* | 1/2009 | Brenner | ................. | G02B 7/001 248/176.1 |
| 2013/0175412 A1* | 7/2013 | Schutz | ................... | G02B 21/24 248/123.2 |
| 2013/0206933 A1* | 8/2013 | Schutz | ............... | F16M 11/2092 248/123.2 |
| 2013/0206934 A1* | 8/2013 | Schutz | ................... | G02B 7/001 248/123.2 |
| 2018/0095234 A1* | 4/2018 | Nakamura | ............. | A61B 90/25 |

* cited by examiner

STAND APPARATUS FOR SURGICAL MICROSCOPE

BACKGROUND OF THE INVENTION

1. Field of the Invention

The present invention relates to a stand apparatus for a surgical microscope.

2. Description of Related Art

A surgical microscope is used in, for example, neurosurgical operations. The surgical microscope is supported on a stand apparatus installed on the floor of an operating room. The stand apparatus includes a vertical parallel linkage that is attached to the stand apparatus with a rotation shaft that is set at a vertical intermediate part of the parallel linkage.

An upper link of the parallel linkage is extended frontward to serve as a support arm whose front end supports the surgical microscope. A lower link of the parallel linkage is extended oppositely (rearward) to support a counterweight. The counterweight cancels the weight of the surgical microscope so that, when the parallel linkage is tilted frontward to move the surgical microscope frontward, the surgical microscope stops stationarily at the moved position. Namely, the counterweight maintains a balanced state of the surgical microscope at a given position. A related art concerning such a stand apparatus is disclosed in, for example, Japanese Patent Publication No. 4628060 (Patent Literature 1).

SUMMARY OF THE INVENTION

The related art movably supports the parallel linkage on the stand apparatus through the rotation shaft set at a vertical intermediate position of the parallel linkage. Accordingly, when the surgical microscope is moved frontward by slanting frontward a section of the parallel linkage above the rotation shaft, the counterweight installed on a lower section of the parallel linkage protrudes oppositely (rearward). This hinders an assistant of a surgeon from standing just behind the stand apparatus.

In consideration of the problem of the related art, the present invention provides a stand apparatus for a surgical microscope, capable of preventing the counterweight from protruding rearward even if the upper section of the parallel linkage is tilted frontward.

According to an aspect of the present invention, the stand apparatus includes a parallel linkage including a front arm, a rear arm, an upper arm, and a lower arm, the front and rear arms being extended in an up-down direction structurally in parallel with each other, the upper and lower arms being extended in a front-rear direction structurally in parallel with each other, each end of the front, rear, upper, and lower arms being rotatably connected to another one through a joint, the joint at a lower end of the front arm being rotatably attached to a stand body of the stand apparatus set on a floor. The stand apparatus also includes a support arm extended frontward from the upper arm over the joint thereof, a front end of the support arm supporting an intermediate part of an end arm, a lower end of the end arm supporting the surgical microscope. Also included are an additional lower arm and an additional rear arm, the additional lower arm being arranged below the lower arm and having a front end rotatably attached to the stand body, the additional rear arm being structurally the same in length and parallelism as a straight line connecting between the front end of the lower arm and the front end of the additional lower arm, ends of the additional rear arm being rotatably connected each through a joint to rear ends of the lower arm and additional lower arm, respectively, to make the lower arm and additional lower arm parallel with each other, the rear end of the additional lower arm being provided with a counterweight. Also included is a crank member supported at the joint from where the support arm is extended, the crank member integrally having a vertical lever extended upward from the joint and a horizontal lever extended rearward from the joint at a predetermined angle with respect to the vertical lever. Further included are a rear sub-arm connecting between a rear end of the horizontal lever and a part of the stand body, the rear sub-arm being structurally the same in length and parallelism as the front arm, a support sub-arm connecting between an upper end of the vertical lever and an upper end of the end arm, the support sub-arm being structurally the same in length and parallelism as the support arm, a compression spring arranged along the rear sub-arm, the compression spring linearly expanding and contracting along the rear sub-arm, and a stopper arranged on the front arm, to stop a lower end of the compression spring. When the front arm is tilted frontward, the stopper is displaced relative to the rear sub-arm, to contract the compression spring, thereby generating a repulsive force acting opposite to the tilted direction.

DESCRIPTION OF PREFERRED EMBODIMENTS

Figure 1:
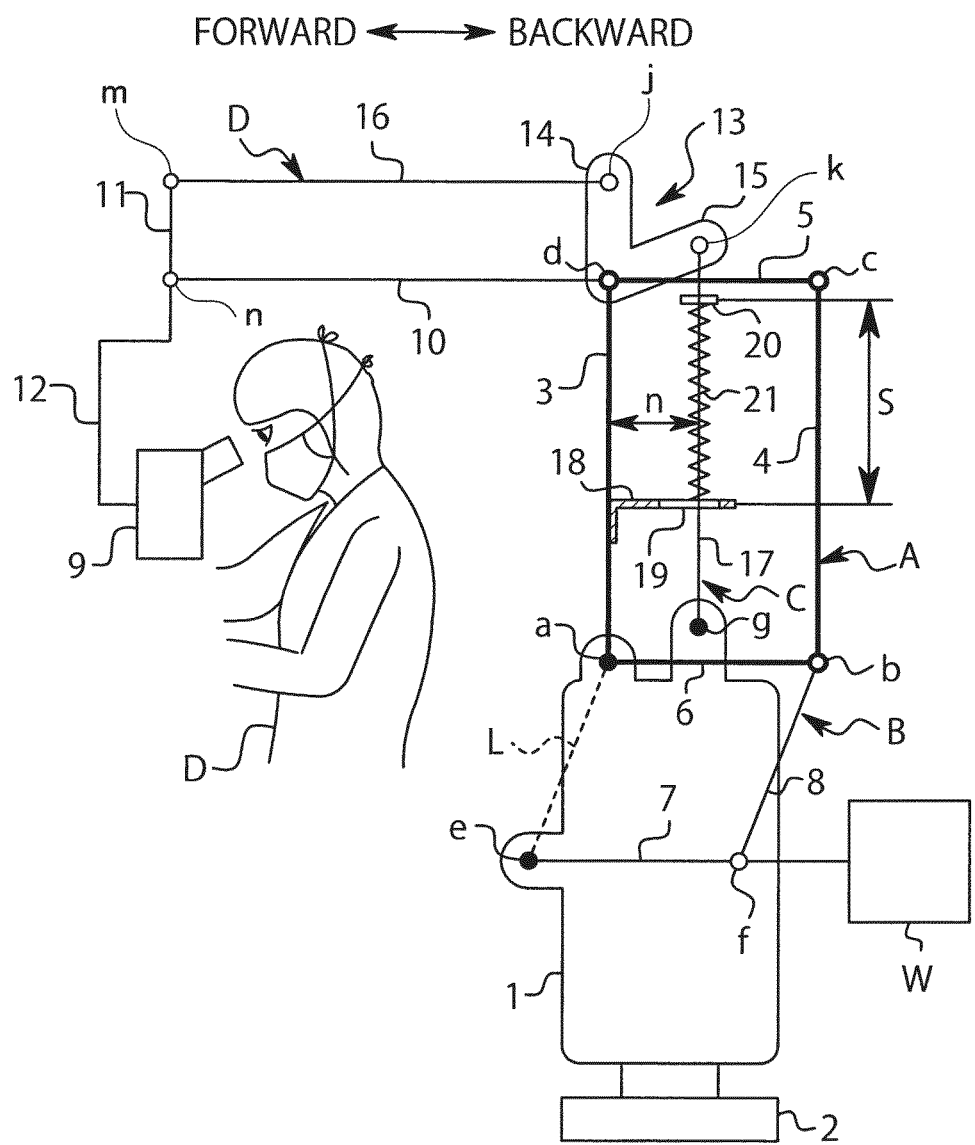
FIG. 1 is a structural view illustrating a stand apparatus for a surgical microscope according to an embodiment of the present invention.

A stand apparatus for a surgical microscope according to an embodiment of the present invention will be explained with reference to FIGS. 1 to 4. Through the drawings and explanation, frontward and rearward directions are as illustrated in FIG. 1.

The stand apparatus includes a stand body 1 set on the floor of an operating room or the like. The stand body 1 has a base 2 on which the stand body 1 is able to turn around a vertical axis.

The stand body 1 includes a parallel linkage A. The parallel linkage A includes a front arm 3 and a rear arm 4 that are extended in an up-down direction and an upper arm 5 and a lower arm 6 that are extended in a front-rear direction. The arms 3 to 6 are rotatably connected to one another through joints a to d. The parallel linkage A (a-b-c-d) is attached to the stand body 1 through a joint a that is at a lower end of the front arm 3, so that the parallel linkage A is able to turn and move relative to the stand body 1.

Arranged under the lower arm 6 is an additional lower arm 7 having a front end e that is rotatably attached to the stand body 1. A joint b at a rear end of the lower arm 6 is connected through an additional rear arm 8 to a joint f at a rear end of the additional lower arm 7. The joints b and f are rotatable. The additional rear arm 8 is structurally the same in length and parallelism as a straight line L connecting between the front end a of the lower arm 6 and the front end e of the additional lower arm 7. This results in forming an additional parallel linkage B that is connected through a shared virtual link a-b to the parallel linkage A. "Structurally the same in length and parallelism" means that the segment (as a link element) between the ends b and f of the additional rear arm 8 and the segment (straight line) L between the ends a and e of the arms 6 and 7 are in parallel with each other and have the same length in practice and that a shape of an intermediate portion of the additional rear arm 8 is allowed to be curved or the like. Accordingly, the link elements d-c, a-b, and e-f are always in parallel with one another.

Attached to the rear end of the additional lower arm 7 is a counterweight W to maintain weight balance for a surgical microscope 9. The counterweight W is chosen in advance according to the weight of the surgical microscope 9.

The upper arm 5 of the parallel linkage A is integral with a support arm 10. A section behind the joint d is the upper arm 5 and a section in front of the joint d is the support arm 10. A main axis of the upper arm 5 agrees with a main axis of the support arm 10, and therefore, the joints c, d, and n are always aligned on a straight line. A front end of the support arm 10 rotatably supports an intermediate part of an end arm 11. A lower end of the end arm 11 supports a suspension arm 12 substantially having a C-shape. The suspension arm 12 supports the surgical microscope 9.

The joint d of the parallel linkage A, which is a start point of the support arm 10, supports a crank member 13. The crank member 13 integrally includes a vertical/longitudinal lever 14 extending upward from the joint d and a horizontal/transverse lever 15 extending rearward from the joint d and forming an angle of 60 degrees relative to the vertical lever 14. In the crank member 13, virtual links d-j and d-k are positionally fixed relative to each other to fix the angle between them. Accordingly, the crank member 13 works as a link angle changing mechanism with respect to the joint d. The angle between the vertical and horizontal levers 14 and 15 is not limited to 60 degrees. It may be 90 degrees or any other.

An upper end of the vertical lever 14 of the crank member 13 is connected to an upper end of the end arm 11 through a support sub-arm 16 that is structurally the same in length and parallelism as the support arm 10. The support arm 10, support sub-arm 16, end arm 11, and vertical lever 14 work as link elements of a parallel linkage D (d-j-m-n).

Arranged between a front end of the horizontal lever 15 (d-k) of the crank member 13 and a part of the stand body 1 is a rear sub-arm 17 (g-k) that is structurally the same in length and parallelism as the front arm 3 (a-d). A lower end g of the rear sub-arm 17 is higher than the lower end a of the front arm 3. The position of the lower end g of the rear sub-arm 17 is based on the angle of the horizontal lever 15. In the drawings, the joints g, a, and e are illustrated each with a black dot to indicate that each is fixed to the stand body 1. The other joints each illustrated with a white dot are not fixed to the stand body 1 and are movable.

The rear sub-arm 17, front arm 3, horizontal lever 15, and an upper part of the stand body 1 work as link elements of a parallel linkage C (g-k-d-a). The upper part positions between the lower the lower end a of the front arm 3 and the lower end g of the rear sub-arm 17. The virtual link a-g of the parallel linkage C is positionally fixed to the stand body 1, and therefore, the crank member 13 maintains a constant state and is not rotatable. Since the crank member 13 is not rotatable and the horizontal lever 15 thereof keeps a constant inclination angle, the end arm 11 always maintains a vertical position. As a result, the suspension arm 12 and surgical microscope 9 are always vertical, and therefore, a doctor D is able to easily conduct observation with the surgical microscope 9. If there is a need of changing the orientation of the surgical microscope 9, a mechanism (not illustrated) arranged at a lower end of the suspension arm 12 will be used.

A stopper 18 is arranged at a lower part of the front arm 3. The stopper 18 has a long through hole 19 elongated in the front-rear direction to pass the rear sub-arm 17 therethrough. A nut 20 is arranged at an upper part of the rear sub-arm 17. The position of the nut 20 is adjustable up and down along the rear sub-arm 17. Between the nut 20 and the stopper 18, a compression spring 21 is arranged along the rear sub-arm 17. The diameter of the compression spring 21 is smaller than that of the nut 20 and greater than the width of the through hole 19, and therefore, the compression spring 21 stays between the nut 20 and the through hole 19. Adjusting the position of the nut 20 along the rear sub-arm 17 results in precisely adjusting an initial length of the compression spring 21.

Figure 2:
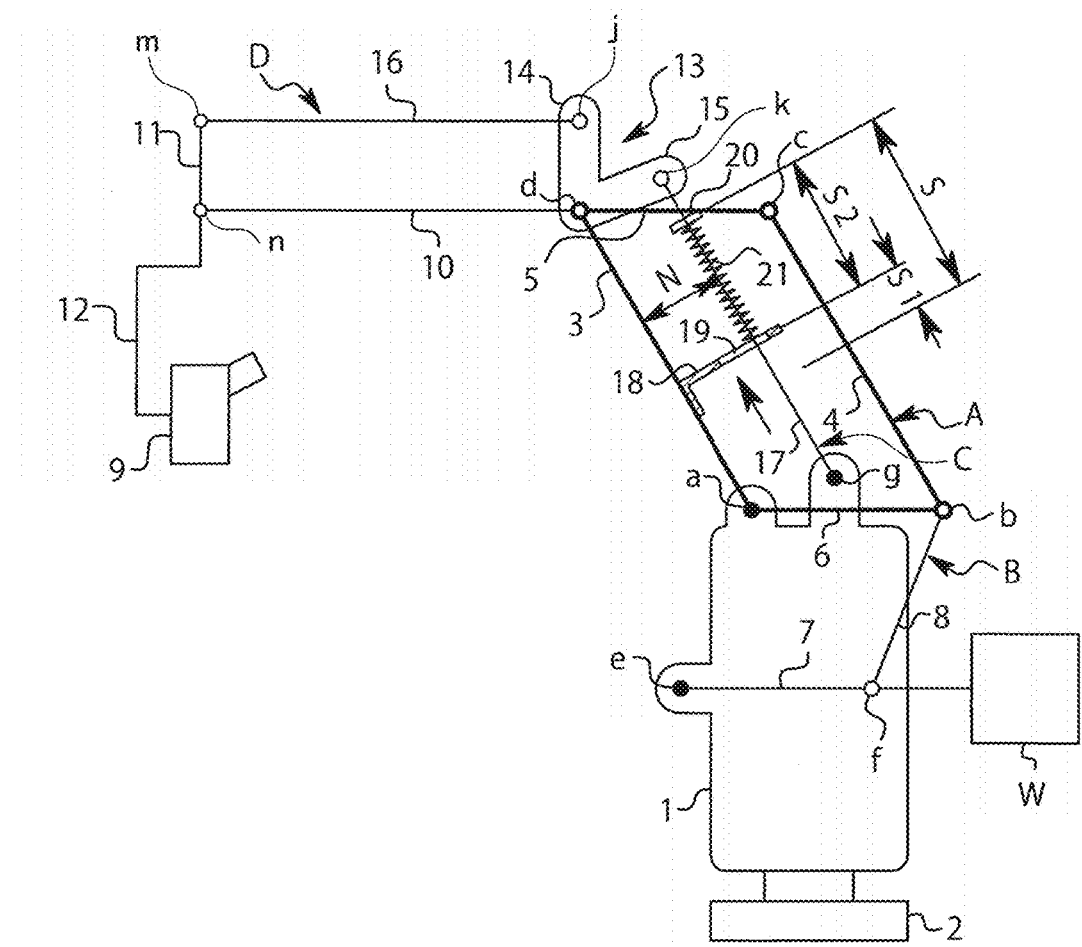
FIG. 2 is a structural view illustrating a frontward tilted state of a parallel linkage of the stand apparatus.

Frontward movement of the surgical microscope 9 will be explained with reference to FIG. 2.

When the surgical microscope 9 is moved frontward, the parallel linkage A inclines frontward. Unlike the related art that supports a vertical intermediate position of the parallel linkage A with the stand body 1, the embodiment supports the parallel linkage A with the lower joint a fixed relative to the stand body 1. As a result, the parallel linkage A as a whole inclines frontward, and therefore, no part of the parallel linkage A protrudes rearward. Namely, the states of the additional lower arm 7 and counterweight W below the parallel linkage A are not affected by the lateral movement of the parallel linkage A. Accordingly, an assistant is able to stand just behind the stand body 1 and help an operation conducted by the doctor D.

Since the additional lower arm 7 is positioned frontward relative to the lower arm 6, the counterweight W is positioned closer to the stand body 1. This configuration prevents the counterweight W from protruding rearward.

When the parallel linkage A is tilted frontward, weight balance thereof is maintained by, instead of the counterweight W, the compression spring 21 arranged along the rear sub-arm 17. The diameter of the compression spring 21 is greater than the width of the through hole 19 formed in the stopper 18, and therefore, the lower end of the compression spring 21 is supported by the periphery of the through hole 19. In an upright state of the parallel linkage A (FIG. 1) before tilting the same frontward, the compression spring 21 has a predetermined length S.

When the parallel linkage A is tilted frontward from the upright state, a relative displacement S1 occurs between the stopper 18 of the front arm 3 and the rear sub-arm 17. For the relative displacement S1, the stopper 18 lifts the lower end of the compression spring 21 to contract the compression spring 21 to a compressed length S2. As a result, the compression spring 21 generates a repulsive force to maintain the balanced state of the frontward tilted parallel linkage A. The relative displacement S1 increases in proportion to an increase in a frontward rotation angle of the parallel linkage A, to increase the repulsive force. Accordingly, the weight balance is properly maintained at any operable rotation angle, to keep the surgical microscope 9 at an optional frontward moved position.

When the parallel linkage A is tilted frontward, a distance n between the front arm 3 and the rear sub-arm 17 changes. At this time, the rear sub-arm 17 is able to move along the through hole 19 because the through hole 19 is elongated. In particular, the lower end g of the rear sub-arm 17 is higher than the lower end a of the front arm 3, and therefore, tilting the parallel linkage A frontward results in widening the distance between the front arm 3 and the rear sub-arm 17 from n to N. Due to the widening of the distance, the front arm 3 and rear sub-arm 17 are sufficiently tilted frontward without interference between them.

Figure 3:
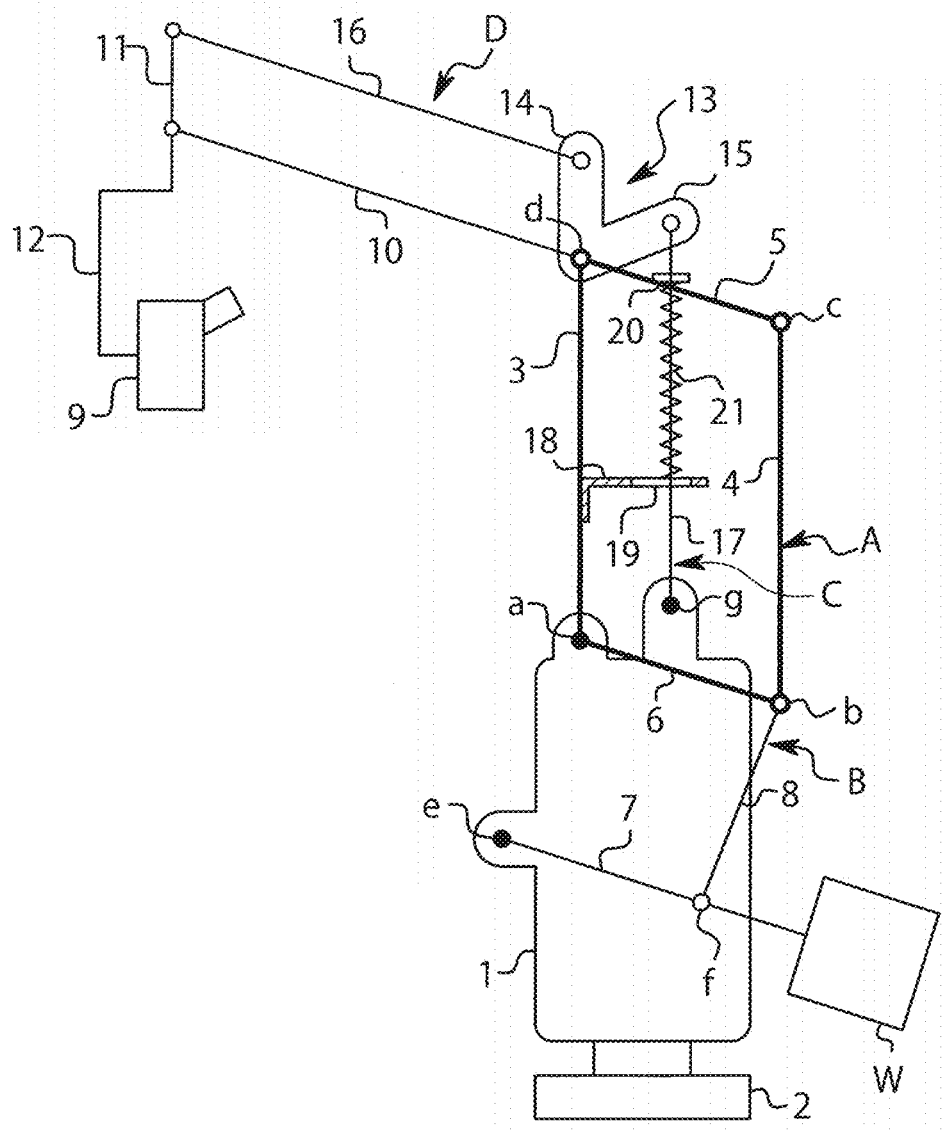
FIG. 3 is a structural view illustrating a lifted state of a support arm of the stand apparatus.
Figure 4:
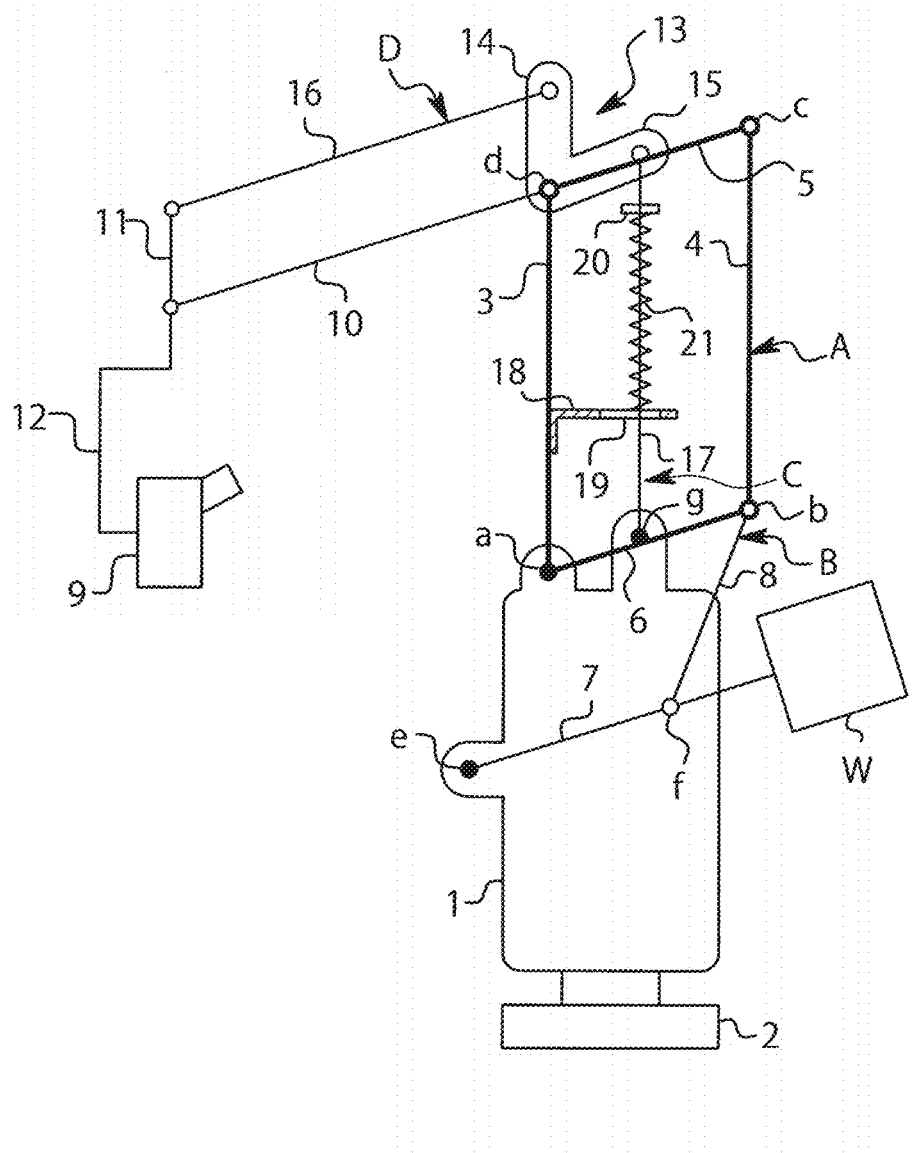
FIG. 4 is a structural view illustrating a lowered state of the support arm.

Upward or downward movement of the surgical microscope 9 will be explained with reference to FIGS. 3 and 4.

When the surgical microscope 9 is moved upward or downward by moving the support arm 10 upward or downward, the parallel linkage A causes the upper arm 5 and lower arm 6 to incline at the same angle. Since the lower arm 6 is connected through the additional rear arm 8 to the additional lower arm 7, the additional lower arm 7 also inclines at the same angle at which the lower arm 6 inclines. As results, the counterweight W fixed relative to the additional lower arm 7 moves downward or upward opposite to the moving direction of the surgical microscope 9. At this time, the counterweight W moves along a vertical arc according to the upward or downward movement of the support arm 10 and never protrudes rearward.

Torque around the axis d due to the weight of the surgical microscope 9 is canceled through the parallel linkages A and B by torque around the axis e caused due to the counterweight W. Accordingly, after the upward or downward movement, the surgical microscope 9 stops at the moved position.

In the stand apparatus according to the embodiment, the counterweight W is attached to the additional lower arm 7 that is positioned below the parallel linkage A, and therefore, the position of the center of gravity of the stand apparatus as a whole is low to stabilize the stand apparatus.

According to an aspect of the present invention, the parallel linkage A is attached with the lower end a to the stand body 1, unlike the related art that attaches a vertical intermediate part of the parallel linkage A to the stand body 1. This configuration prevents, when the parallel linkage A is tilted frontward, any part of the parallel linkage A from protruding rearward. When the support arm 10 is moved upward or downward, the counterweight W only moves downward or upward without protruding rearward. As results, an assistant is able to stand just behind the stand body 1 and conduct assisting work.

Weight balance of the frontward tilted parallel linkage A is maintained by, instead of the counterweight W, the compression spring 21 arranged along the rear sub-arm 17. When the parallel linkage A is tilted frontward, the stopper 18 causes a relative displacement to contract the compression spring 21. This produces a repulsive force to maintain the frontward tilted state of the parallel linkage A.

The counterweight W is attached to the additional lower arm 7 that is lower than the parallel linkage A, and therefore, the position of the center of gravity of the stand apparatus as a whole is low to stabilize the stand apparatus.

According to another aspect of the present invention, the additional lower arm 7 is positioned ahead of the lower arm 6, and therefore, the position of the counterweight W becomes closer to the stand body 1. This configuration is effective to prevent the counterweight W from protruding rearward.

According to still another aspect of the present invention, the rear sub-arm 17 is positioned higher than the front arm 3, and therefore, tilting the parallel linkage A frontward results in extending a distance between the front arm 3 and the rear sub-arm 17, thereby causing no interference between the arms 3 and 17.

This patent application claims the benefit of priority under 35 U.S.C. 119(a) to Japanese Patent Applications No. 2016-192813 filed on Sep. 30, 2016 and No. 2016-236371 filed on Dec. 6, 2016 whose disclosed contents are cited herein.

What is claimed is:

1. A stand apparatus for a surgical microscope, the stand apparatus comprising:
   a parallel linkage including a front arm, a rear arm, an upper arm, and a lower arm, the front and rear arms being extended in an up-down direction structurally in parallel with each other, the upper and lower arms being extended in a front-rear direction structurally in parallel with each other, each end of the front, rear, upper, and lower arms being rotatably interconnected to one another via a plurality of joints, and a first joint, among the plurality of joints, at a lower end of the front arm being rotatably attached to a stand body of the stand apparatus set on a floor;
   a support arm extended frontward from the upper arm over a second joint, among the plurality of joints, that connects the upper arm and the front arm, a front end of the support arm supporting an intermediate part of an end arm, wherein a lower end of the end arm is configured to support the surgical microscope;
   an additional lower arm and an additional rear arm, the additional lower arm being arranged below the lower arm and having a front end rotatably attached to the stand body, the additional rear arm being structurally the same in length and parallelism as a straight line connecting between the front end of the lower arm and the front end of the additional lower arm, a first end of the additional rear arm being rotatably connected to a rear end of the lower arm via a third joint among the plurality of joints and a second end of the additional rear arm being rotatably connected to a rear end of the additional lower arm via a fourth joint among the plurality of joints such that the lower arm and additional lower arm are interconnected parallel with each other, and wherein the rear end of the additional lower arm is provided with a counterweight;
   a crank member supported at the third joint from which the support arm extends, the crank member integrally having a vertical lever extended upward from the third joint and a transverse lever extended rearward from the third joint at a predetermined angle with respect to the vertical lever;
   a rear sub-arm connecting between a rear end of the horizontal lever and a part of the stand body, the rear sub-arm being structurally the same in length and parallelism as the front arm;
   a support sub-arm connecting between an upper end of the vertical lever and an upper end of the end arm, the support sub-arm being structurally the same in length and parallelism as the support arm;
   a compression spring arranged along the rear sub-arm, the compression spring linearly expanding and contracting along the rear sub-arm; and
   a stopper arranged on the front arm to support a lower end of the compression spring, wherein:
   when the front arm is tilted frontward, the stopper is displaced relative to the rear sub-arm, to contract the compression spring, thereby generating a repulsive force acting opposite to the tilted direction.

2. The stand apparatus of claim 1, wherein the front end of the additional lower arm is positioned ahead of the front end of the lower arm.

3. The stand apparatus of claim 1, wherein the lower end of the rear sub-arm is positioned higher than the lower end of the front arm.

\* \* \* \* \*